(12) United States Patent
Skarping et al.

(10) Patent No.: US 8,034,624 B2
(45) Date of Patent: Oct. 11, 2011

(54) SAMPLING DEVICE

(75) Inventors: Gunnar Skarping, Hässleholm (SE); Marianne Dalene, Hässleholm (SE)

(73) Assignee: Provtagaren AB, Hassleholm (SE)

( * ) Notice: Subject to any disclaimer, the term of this patent is extended or adjusted under 35 U.S.C. 154(b) by 50 days.

(21) Appl. No.: 12/299,940

(22) PCT Filed: May 8, 2007

(86) PCT No.: PCT/SE2007/000451
§ 371 (c)(1),
(2), (4) Date: Dec. 9, 2008

(87) PCT Pub. No.: WO2007/129965
PCT Pub. Date: Nov. 15, 2007

(65) Prior Publication Data
US 2009/0117663 A1    May 7, 2009

Related U.S. Application Data

(60) Provisional application No. 60/798,502, filed on May 8, 2006.

(51) Int. Cl.
*G01N 33/00* (2006.01)
(52) U.S. Cl. ....... 436/109; 422/82.05; 422/85; 436/106; 436/127; 436/139; 436/171; 436/172
(58) Field of Classification Search .......... None
See application file for complete search history.

(56) References Cited

U.S. PATENT DOCUMENTS
4,273,556 A * 6/1981 Gindler .......... 436/108

FOREIGN PATENT DOCUMENTS
GB    1163647 A    9/1969
WO    WO 00/75622 A1    12/2000

OTHER PUBLICATIONS

Zweigbergk et al. "Development of a diffusive sampling method for determination of methyl isocyanate in air". 2002. J. Environ. Monit. vol. 4, pp. 663-666.*
Kormos et al. "Determination of Isocyanates in Air by Liquid Chromatography with Fluorescence Detection". 1981. Anal. Chem. vol. 53. pp. 1122-1125.*
Eickeler, E., Aspects of quality assurance in the determination of 2,4-toluene diisocyanate by HPLC, *Fresenius J. Anal. Chem.*, vol. 336, (1990) pp. 129-131.
Guglya, E.B. et al., Determination of Isocyanates in Air, *Journal of Analytical Chemistry*, vol. 55, No. 6, (2000) pp. 508-529.
Molander, P., Isocyanates, in Chromotographic Analysis of the Environment, edited by Leo M.L. Nollet, Boca Raton: Taylor & Francis Group, (2006) pp. 779-802.

* cited by examiner

*Primary Examiner* — Yelena G Gakh
*Assistant Examiner* — David Weisz
(74) *Attorney, Agent, or Firm* — Weingarten, Schurgin, Gagnebin & Lebovici LLP (57) ABSTRACT

A sampling device for analysis of a substance which is chosen from the group consisting of isocyanates, aminoisocyanates, amines, and isothiocyanates, and which is present in an air flow intended to pass through the sampling device is disclosed, as well as a method for the production of said sampling device, and a method for the analysis of said substance in the air flow.

36 Claims, 3 Drawing Sheets

1:  reference
2:  ICA
3:  reference

1: reference
2: ICA
3: reference

US 8,034,624 B2

SAMPLING DEVICE

This application is a §371 national phase filing of PCT/SE2007/000451, filed May 8, 2007, and claims priority to U.S. Provisional Application No. 60/798,502 filed May 8, 2006.

FIELD OF THE INVENTION

The present invention relates to a sampling device for analysis of a substance which is chosen from the group consisting of isocyanates, aminoisocyanates, amines, and isothiocyanates, and which is present in an air flow intended to pass through the sampling device, to a method for the production of said sampling device, and to a method for the analysis of said substance in the air flow.

BACKGROUND ART

Polyurethane (PUR) products frequently occur in industry, in particular in manufacturing and handling polyurethane foam, elastomers, adhesives and lacquers. Polyurethane is produced by the reaction of a bifunctional isocyanate with a polyfunctional alcohol. The satisfactory technical qualities of polyurethane have resulted in a large increase of its use and application fields during the last decade. In connection with thermal decomposition of polyurethanes, however, the formation of isocyanates, aminoisocyanates and amines might occur, and extremely high contents can be found in air, e.g. when welding automobile sheet steel. Besides the known types of isocyanate, also new types of aliphatic isocyanates have been detected, in connection with e.g. heat treatment of car paint. Most of the isocyanates formed have been found to be represented by so-called low molecular isocyanates. During short periods of heating, as is the case when welding, particularly high contents of isocyanates may be present (peak exposure). Of all the dangerous substances on the limit value list, isocyanates have the lowest permissible contents. Exposure to this new type of isocyanates was previously unheard of. Isocyanates in both gas and particle phase have been detected in connection with welding, grinding and cutting of painted automobile sheet steel, and respirable particles in high contents containing isocyanates have been detected. In thermal decomposition products of painted automobile sheet steel, detection has been made of, among other things, methyl isocyanate (MIC), ethyl isocyanate (EIC), propyl isocyanate (PIC), phenyl isocyanate (Phi), 1,6-hexamethylene diisocyanate (HDI), isophorone diisocyanate (IPDI), 2,4- and 2,6-diisocyanate toluene (TDI) and 4,4-methylene diphenyl-diisocyanate (MDI).

In thermal decomposition of phenol/formaldehyde/urea (FFU) plastic, isocyanic acid and methyl isocyanate are formed. FFU plastic is used, among other things, in wood glue and as a binder in mineral wool (and bakelite), which is frequently used as insulation for ovens and furnaces in industrial and domestic use. New fields of application in which exposure to isocyanates has been detected are the soldering and processing of printed circuit boards in the electronic industry, the welding, grinding and cutting of painted sheet steel in the automobile industry and the welding of lacquered copper pipes. Isocyanates have a varying degree of toxicity to the organism depending on their chemical and physical form. As a result, the hygienic limit values have been set at an extremely low level in all countries. For the exposed individual, the degree of exposure to isocyanates varies considerably in different operations during a working day and in connection with breakdowns. Thermal decomposition products from PUR constitute a special problem, since new and completely unknown isocyanates are formed, whose toxicity has not yet been analyzed in a satisfactory manner. Furthermore, the increasingly sophisticated measuring methods have revealed exposure to isocyanates in an increasing number of operations in industry.

To sum up, there are a number of operations in numerous working areas where people are daily exposed to or at risk being exposed to isocyanates at a varying degree. Considering the ominous tendency of isocyanates to cause respiratory diseases and the fact that there are some carcinogenic substances among the thermal decomposition products of polyurethane, e.g. 2,4-diamine toluene (TDA), 4,4-methylene diamine (MDA) and MOCA, it is very important to measure in a reliable, sensitive and rapid manner any presence of isocyanates, but also other decomposition products dangerous to health, in environments where there is such a risk.

Several commercially available direct reading instruments for isocyanates and other reactive organic and inorganic compounds are known. One type is based on a principle where e.g. air containing isocyanates is sucked through a cellulose filter paper. The filter paper (filter-tape) is impregnated with reagents. The result of the reaction between e.g. isocyanates and the reagents is that a color is formed (see references 1-7). The intensity of the color depends on the air concentration of e.g. isocyanates.

The measuring principle is based on a light source emitting light (of a certain wave length) to the impregnated filter tape. Then a detector measures the reflected light. The color formation with time on the impregnated filter is proportional with the air concentration of e.g. isocyanates. Such commercially available instruments are either static or dynamic. In the static instruments the impregnated filter is put on in the measuring device and the air concentration can be measured either by visual observation by comparison with a colored reference. In the dynamic measuring devices the tape is static for a certain period of time (typically 2 minutes) and thereafter the filter is moved and a new fresh filter is placed in the sucking zone.

These instruments typically provide continuous air monitoring of e.g. isocyanates and the air concentration can be instantaneously monitored. The measuring devices can be hand held or stationary. The measuring device needs to be calibrated for the compound that is to be measured. There may be interferences if several compounds are present in air.

Drawback with Current Techniques:

There are several drawbacks with the present types of instruments. One major drawback is that the response may vary if the compounds to be measured are present in particle form. Gas phase compounds will form a homogeneous color over the sampling spot on the filter whereas compounds in particle form will have a non homogenous color on the filter. Particles will create spots of more intense color on the filter. In addition droplets (particles) will impact on the filter resulting in incomplete reaction between the compounds to be measured and the reagent as the reagent and the compounds in the particles will not efficiently mix. The air levels will be underestimated. In fact, the principle does not correctly work for particle borne compounds.

The measurements of compounds in gas phase are basically more relevant, but still considerable limitations are present. If the air contains particles (such as soot and smoke) the particles will deposit on the filter. The measuring principle has the drawback that reflected light will be affected also by other compounds/particles that are deposited on the filter. Further, some isocyanates in the gas phase, such as methyl isocyanate ($CH_3NCO$) and isocyanic acid (HNCO), will pass through the filter (breakthrough) and will therefore not react with the reagent and form a color and will not be detected (see references 1 and 2). Another drawback is that the color reaction will not only take place on the surface of the filter but also on deeper layers (and the backside) but it is only the color on the surface that is measured (detection losses). In addition, the reaction depends on the air humidity. If the air is very dry, the formation of color will be slow and much less color is formed as compared to humid air. Sufficient air humidity is critical for correct estimation of air concentration (see reference 1). The color formed for low molecular weight isocyanates with the old technique is not permanent which results in an unsatisfactory low sensitivity.

Further, it would be of interest to detect smaller hazardous compounds, e.g. smaller isocyanates, in a reliable and also quicker way than hereto known.

In view of this, there is a great demand for an improved sampling device and an improved method for sampling of products dangerous to health, such as isocyanates, aminoisocyanates, amines, and isothiocyanates, in a rapid, reliable, precise and tamper proof manner.

SUMMARY OF THE INVENTION

The object of the present invention is to provide an improved device and an improved method for analysis of a substance selected from the group consisting of isocyanates, aminoisocyanates, isothiocyanates, and amines. This object is achieved with a sampling device having the features defined in independent claim 1 and with a method for analysis of said substance as defined in independent claim 21.

Further features are defined in the dependent claims, respectively.

In one aspect, the present invention refers to a sampling device as defined in independent claim 1.

In another aspect, the present invention refers to a method for analysis of a substance as defined in independent claim 21.

In a further aspect, the present invention refers to a method for the preparation of said sampling device as defined in independent claim 20.

In still another aspect, the present invention refers to a kit as defined in present claim 19.

In still another aspect, the present invention relates to a pad impregnated with the reagent, as defined in independent claim 24.

BRIEF DESCRIPTION OF THE DRAWINGS

FIG. 1 shows schematically one embodiment of the sampling device according to the present invention. An air flow 1 containing the substances, also called analytes herein, to analyse is brought to pass through a cylindrical adsorbent device 2 having a sorbent surface 3 on its inner wall. Substances in the gaseous phase of the air flow 1 are reacted on the sorbent surface 3 creating a color reaction, which is measured and detected by use of a light source 4 and a detector 5, respectively. Substances in the particle phase of the air flow are collected on an end filter device 6 in the lower end of the sampling device. The air flow 1 through the sampling device is provided with a pump or suction device 7.

DETAILED DESCRIPTION OF PREFERRED EMBODIMENTS

The sampling device according to the present invention, primarily intended to be a direct reading device for analysis of gas phase air borne reactive compounds, is based on pump assisted active diffusive sampling for direct and continuous indication of certain reactive organic and inorganic compounds. Colorimetric measurements are made on a sorbent surface that has been impregnated with one or more reagents and one or more color reaction developing agents, which during reaction with the substances in the air flow forms a color that can be indicated by a light source and a detector for reflected light. Light in the wavelength range 300-800 nm, preferably 470-550 nm, is used. Reactions between other reagents and analytes in this context are known in references 1-6, and reagents in the form of volatile primary and secondary amine compounds are disclosed more in detail in WO 00/75622, an earlier patent application filed by the present applicant (see also references 1 and 2).

Figure 1:
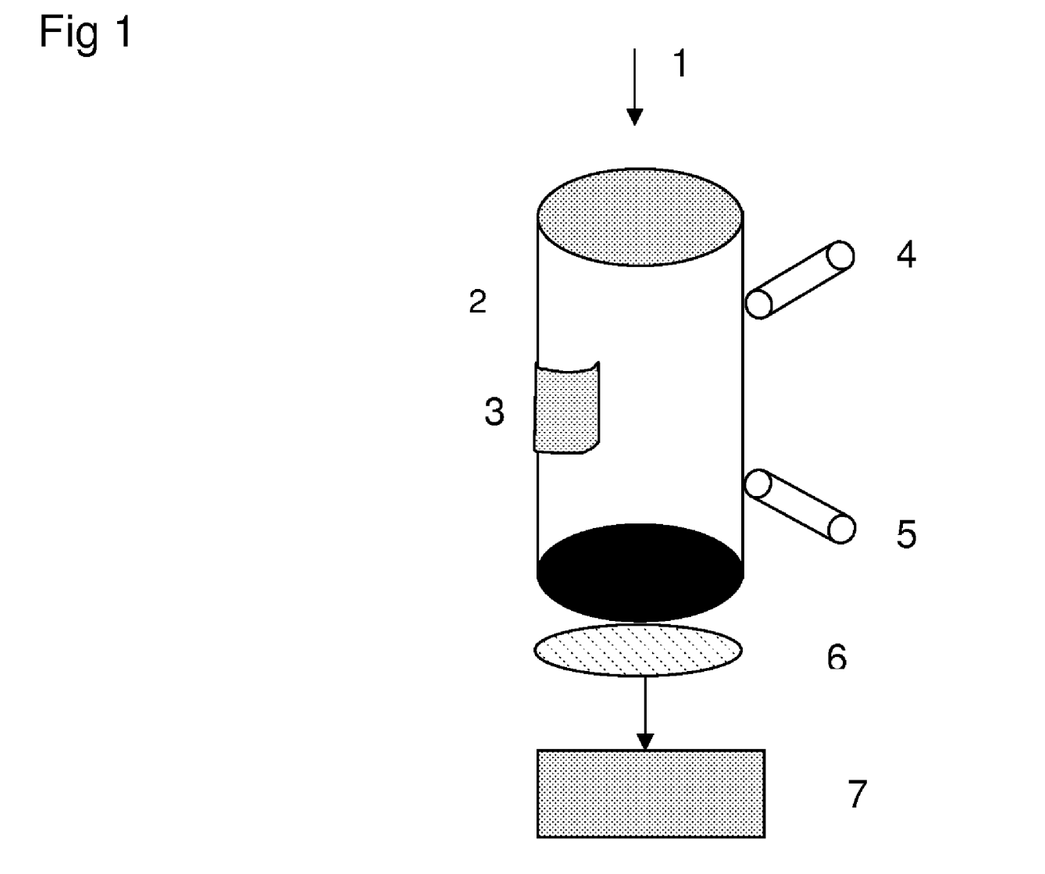

As shown in the embodiment in FIG. 1, the sampling device is connected to a pump or suction device 7 that sucks an air flow 1 through an inlet into an adsorption device 2, the interior of and an outlet of the sampling device, e.g. in the form of a cylindrical tube, with a certain air flow rate. Any conventional pump may be used. On the inner side wall of the adsorbent device 2 a sorbent surface 3 impregnated with at least one reagent and at least one color reaction developing agent is provided. The sorbent having an impregnated surface may be made of cellulose, silica, RP-18 coated silica, cotton fibre, glass fibres, polyether, polystyrene divinylbenzene, teflon, agarose, polyacrylamide or any other convenient material. During the sampling for the analysis, a representative portion of gas phase molecules are deposited on the sorbent surface 3, whereupon a reaction takes place and a color is formed, whereas particles provided with the substances to analyse are collected on an end filter device 6, also impregnated with the said at least one reagent and said at least one color reaction developing agent and normally placed in or close to the outlet end of the adsorbent device 2. The color measurement is made on a certain predetermined region of the sorbent surface. The formation of color with time is proportional to the concentration of the reactive gas, e.g. isocyanates. The light source 4 emitting light having the above-mentioned wavelength interval is arranged at an angle of 10-90° in relation to the sorbent surface 3. The light source 4 may be attached to the sampling device in any conventional way. Any conventional light source may be used, e.g. a light diode or a laser source.

The light reflected on the sorbent surface 3, on which a color reaction has taken place, is detected with a detector 5 arranged at an angle of 10-90° in relation to the sorbent surface 3. The detector 5 may be attached to the sampling device in any conventional way. Any conventional detector may be used, e.g. a photomultiplicator or a photodiode.

After a certain sampling time period the inserted sorbent may be automatically changed to a new one. The tube embodiment of the sampling device is typically 50-200 mm long with an internal diameter of 5-20 mm. The area of the sorbent surface is 0.05-30 $cm^2$, typically 1 $cm^2$. Reference measurements can be performed to an unexposed sorbent surface placed inside or outside the measuring device. The air flow rate used in connection with the present invention is conveniently from 10 ml per minute up to 5000 ml per minute, e.g. from 100 ml per minute up to 1000 ml per minute. The sampling device according to the present invention is not restricted to the tube or cylindrical shape as shown in FIG. 1. Instead, it may also have other forms, e.g. with an oval, rectangular or square cross-section. Further, one or more concentrical forms of surfaces with impregnated sorbent surfaces may be placed within the sampling device.

Moreover, a strip impregnated with the reagent and the color reaction developing agent may be suspended in the adsorbent device 2 of the sampling device, either as a complement to or instead of the sorbent surface 3 on the inner wall.

Further, in another embodiment different sorbent surfaces 3 are arranged on a sheet or a disc which is moved or rotated in such a way that each sorbent surface 3 is contacted during a predetermined time period with the air flow 1 in the adsorbent device 2 via e.g. one or more openings in the inner wall of the adsorbent device 2.

One important difference compared to several known methods is that the air flow with substances to analyze passes the impregnated sorbent surface in a horizontal or essentially horizontal direction, whereas the air flow in several known methods vertically hits the sorbent surface.

The advantages compared to present known techniques are several:

Particles will not deposit on the impregnated sorbent surface 3—no interference from particles in the analysis;

The load of reagent can be much higher, as air is not sucked through the sorbent surface 3;

The air humidity of the sorbent can be made controlled by a humid back-up pad that continuously refreshes the sorbent with humidity;

Several kinds of sorbents can be used as there is no need to take into account the pressure drop as for conventional filters;

The gas to be monitored will mainly react on the surface 3 of the sorbent making detection of reflected light more optimal.

As the sampling device is open, the pressure drop of said device will be minimal. In addition, said device can be used as a sampler for subsequent analysis. The impregnated sorbent and the end filter device 6 can be removed and analyzed at a laboratory. This application will give time resolved automatic air measurements of the amount of analytes in both gas and particle phases (also removing the end filter).

The sampling device has been developed for and can be used for detection of compounds such as: ammonia ($NH_3$), amines: [dimethylamine (DMA) n-butylamine (n-BA), methylene dianiline (MDA), p-phenylene diamine (PPD), 2,4 and 2,6-toluene diamine (TDA), trimethylamine (TMA)]; diisocyanates, cyclohexyl diisocyanate (CHDI), hexamethylene diisocyanate (HDI), dicyclohexyl metan diisocyanate (HMDI), IEM, isophorone diisocyanate (IPDI), 4,4'-methylene diphenylisocyanate (MDI), naphtyidiisocyanate (NDI), paraphenylene diisocyanate (PPDI), 2,4 and 2,6-toluene diisocyanate (TDI), trimethylhexamethylene diisocyanate (TMDI), trimethyl xylene diisocyanate (TMXDI), xylenediisocyanate (XDI); hydrazines: monomethylhydrazine (MMH), hydrazine ($N_2H_4$,) 1,1 dimethylhydrazine (UDMH).

The sampling device can also be used with modification of the color reagent for: Hydrides: [Arsine ($AsH_3$), Diborane ($B_2H_6$), Disilane ($Si_2H_6$), Germane ($GeH_4$), Hydrogen Selenide ($H_2Se$), Phosphine ($PH_3$), Silane ($SiH_4$), Stibine ($SbH_3$), tert-Butylarsine (TBA), tert-Butylphosphine (TBP)], Hydrogen Cyanide (HCN), Hydrogen Sulfide ($H_2S$), Mineral Acids: [Hydrogen Bromide (HBr), Hydrogen Chloride (HCl), Hydrogen Flouride (HF), Hydrogen Iodide (HI), Nitric Acid ($HNO_3$), Sulfuric Acid ($H_2SO_4$)], Oxidizers: [Bromine ($Br_2$), Chlorine ($Cl_2$)—II, Chlorine Dioxide ($ClO_2$), Hydrogen Peroxide ($H_2O_2$), Nitrogen Dioxide ($NO_2$), Ozone ($O_3$)], Phosgene ($COCl_2$), Sulfur Dioxide ($SO_2$).

Depending on the analyte, i.e. isocyanates, aminoisocyanates, amines; or isothiocyanates, to be analysed or monitored in the air flow 1, different new reagents are used. For e.g. isocyanates a group of new reagents has been developed which have the ability to indicate much smaller quantities of airborne small aliphatic isocyanates and also in a much quicker way compared to known techniques. The reagents indicate not only aromatic isocyanates, but also small aliphatic isocyanates like butylisocyanate (BIC), propylisocyanate (PIC), iso-propylisocyanate (i-PIC), ethylisocyanate (EIC), methylisocyanate (MIC) and isocyanic acid (ICA.)

The new reagents according to the present invention comprises metadihydroxy, alkoxy or aryloxy-aromatics.

More precisely, the reagent according to the present invention is an aromatic compound chosen from:

benzene compounds having the structure wherein R=H, $CH_3$, $C_2H_5$, $C_3H_7$, $C_4H_9$, $C_5H_{11}$, $C_6H_{14}$, $C_6H_5$, $C_{10}H_8$, and $X_1$, $X_2$, $X_3$, $X_4$ may be similar or non-similar and is R, OH, OR, COR, CONHR, $CO_2R$, or OCOR, wherein R is as defined above;

naphtalene compounds having the structures wherein R, $X_1$ and $X_2$ are as defined above; k is one or more of such a substituent as H, $SO_3H$, $SO_3Me^+$ ($Me^+=Li^+$, $Na^+$, $K^+$), OH, OR, R, COR, $CO_2R$, $CO_2H$, OCOR, $NO_2$, or SR (wherein R is as defined above);

antracene compounds having the structures wherein R, $X_1$, $X_2$, and k are as defined above;

phenantrene compounds having the structures wherein R, $X_1$, $X_2$, and k are as defined above.

Among the above-mentioned benzenes, dihydroxybenzophenone, 2,3,4-trihydroxybenzophenone, 1,3,5-trihydroxybenzene and 2,4,6-trihydroxylacetophenone have turned out to be preferable.

Among the above-mentioned naphtalenes, 1,3-dihydroxynaphtalene has turned out to be preferable.

Among the above-mentioned antracenes, 1,3-dihydroxyantracene has turned out to be preferable.

Among the above-mentioned phenantrenes, 1,3-dihydroxyphenantrene has turned out to be preferable.

One or more of the reagents listed above may be present at the same time on the sorbent surface 3 of the sampling device. Each reagent is bound to the sorbent surface 3 via hydrogen bonds.

A color reaction developing agent, also called diazoting agent, is also present on the sorbent surface 3 of the sampling device. In one embodiment the color reaction developing agent is an ammonium nitrite compound, i.e. $NH_4NO_2$, or an alkali metal nitrite compound, e.g. $LiNO_2$, $NaNO_2$, or $KNO_2$. The color reaction developing agent is bound via ionic bonds to the sorbent surface 3.

In an alternative embodiment one or more divalent metal ions are also bound to the sorbent surface 3 of the adsorbent device 2, e.g. $Zn^{2+}$, $Co^{2+}$, $Fe^{2+}$, $Cr^{2+}$, $Cu^{2+}$ and $Mg^{2+}$. Thus, said divalent metal ions may be added as a complement to the color reaction developing agent. Further, the sorbent surface 3 of the adsorbent device 2 may be impregnated with one or more different color reaction developing agents, as well as with one or more of the above listed divalent metal ions.

The sorbent surface is completely (100%) saturated with the reagent, and to about 80% saturated with a solution of the color reaction developing agent and, optionally, with a solution of metal salts, respectively.

In one aspect the present invention refers to a method for the reproduction of the sampling device according to the present invention.

The sorbent surface 3 of the adsorbent device 2 in the sampling device may be impregnated in the following way. First the reagent is dissolved in one or more suitable organic solvents, such as acetonitrile, tetrahydrofurane or ethylacetate. In one embodiment up to 35%, preferably 20-30% by volume, of the organic solvent is replaced with an ethylene glycol ether having the formula $RO-(CH_2CH_2O)_nR$, wherein n=0, 1, 2, 3, or 4, and $R=CH_3$ or $C_2H_5$. When the sorbent surface 3 has been impregnated with the reagent dissolved in the organic solvent, the organic solvent is evaporated during a subsequent drying step in air leaving the reagent impregnated on the sorbent surface 3. Thereafter, the color reaction developing agent, such as a buffered solution of ammonium or alkali metal nitrite, is added to the sorbent surface 3, e.g. via spraying, optionally in mixture with one or more divalent metal ions. In another embodiment, the reagent dissolved in the solvent and the color reaction developing agent, optionally also the divalent metal ions, may be added at the same time to the sorbent surface 3, e.g. by spraying. In the latter embodiment, the addition of these components should take place just before the analysis is to be performed, as the sorbent surface 3 should have a high moisture content. Alternatively, when the dissolved reagent has been added first, followed by drying, the color reaction developing agent, optionally also the divalent metal ions, should be added just before the analysis due to the same reasons.

In one aspect the present invention also relates to a method for analysis of a substance chosen from the group consisting of isocyanates, aminoisocyanates, amines, and isothiocyanates. Referring to the embodiment schematically shown in FIG. 1, the following steps take place. When the air flow 1 passing through the adsorbent device 2 of the sampling device, air borne substances therein contacts the impregnated sorbent surface 3, which contains water and is kept moistured, e.g. via a humid back-up pad, on which they are quickly hydrolysed to amines due to the water in the moisture. These amines are diazotised by the color reaction developing agent, i.e. nitrite salts, to diazonium salts (see references 1 and 2). Then these diazonium salts undergo nucleophilic coupling with the ring in the aromatic structures (phenols) of the reagent to give colored azo-compounds (see references 1-6), which then are detected by use of the light source and the detector attached to the sampling device. The color change due to the color reaction may be increased by specific wavelengths by the use of the divalent metal ions, due to their complexing properties with the formed azo-compounds. The reflectance of light is measured from the colored surface. The formed color is related (proportional) to the air concentration of the substance to be analysed. By calibrating the response with a known concentration, the device can measure the substance in question, e.g. isocyanates. The end filter device 6 may contain the same components as the sorbent surface 3 of the adsorption device 2 and may be analysed in the same way or after sampling by measuring the reflectance. The analysis of the end filter device 6 may be performed with the same light source 4 and detector 5 as discussed above, or with another light source and/or detector. Further, the formed colored reaction product can be measured after sampling by direct UV-VIS detection or after chromatographic separation with e.g. thin layer chromatography or liquid chromatography with UV-VIS or mass spectrometric detection.

The term "sorbent surface" used throughout the application text is intended to mean the surface of any sorbent material to be impregnated with the reagent, the color reaction developing agent and, optionally, the divalent metal ions, and on which measurements of reflected light in view of the color intensity is to be made with a view to analyzing whether one or more certain substances to analyses is/are present in the air sample, and, if so, the concentrations thereof.

The term "adsorption device 2" used throughout the application text is intended to mean the part of the sampling device in which the substances to analyse in the gas phase of the air flow passing the adsorption device 2 is to be reacted. The adsorption device contains the sorbent surface 3 in one or more of the modifications disclosed above. In one embodiment the adsorption device is delimited in its lower end by the end filter device 6.

The amount of water in the moistened sorbent is at least 2-40%, preferably 20-30%.

The reagents are applied to the sorbent surface 3 in concentrations of 0.2-20 mg per $cm^2$ of sorbent surface area. The color reaction developing agents are applied in concentrations of 0.01-0.2 mmol per $cm^2$ of sorbent surface area. The divalent metal ions are used in same concentrations as the color reaction developing agents. Another application of the developed color reagent is the indication of isocyanates present on surfaces (ref 7). In that application the reagents are impregnated on pads containing the same kinds of materials as described above for the sampling device embodiment. The stable colored reaction products can visually indicate the presence of the substances to analyse, e.g. isocyanates, by passing an air flow containing the substance to analyse or by contacting the pad with a surface on which the substance to analyse may be present. The formed colored reaction products can also be monitored by chromatography and UV-VIS or mass spectrometric detection. The term "pad" is herein intended to mean any material having a surface which is possible to impregnate with the reagent, the color reaction developing agent, and, optionally, the divalent metal ions, as well as with water.

EXAMPLES

Figure 2:
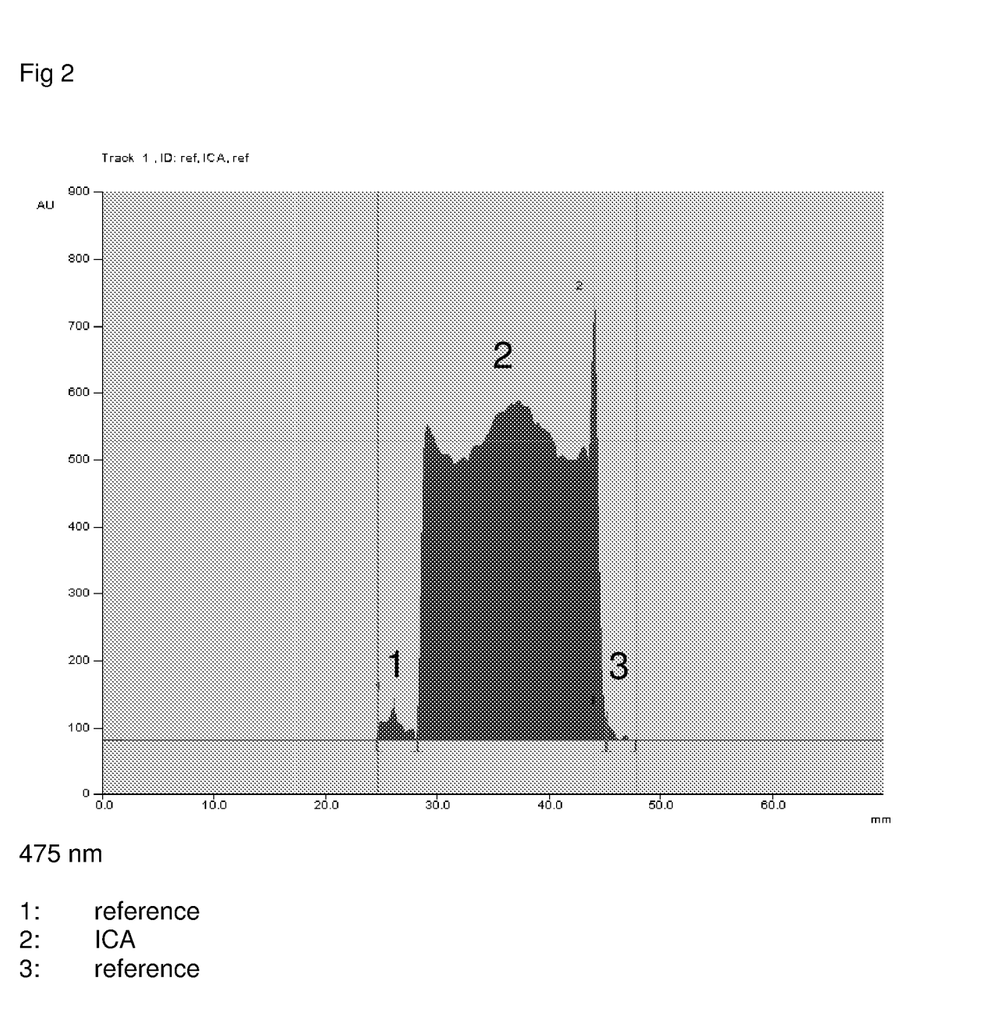
FIG. 2 and FIG. 3 show diagrams from measurement of isocyanic acid (ICA) at 475 nm and 550 nm with 2,4,6-trihydroxyacetophenone as reagent.
Figure 3:
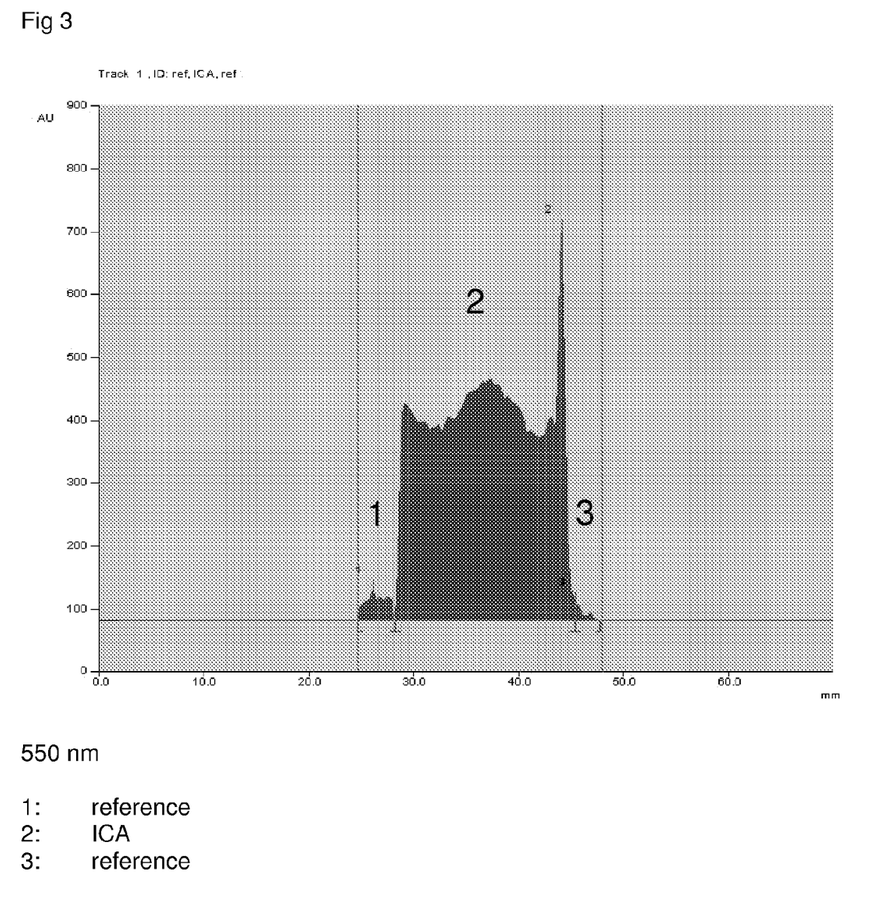

During an experiment a cylindrical sampling device as shown in FIG. 1 was used (length: 100 mm; internal diameter: 20 mm) for the analysis of isocyanic acid in gas phase, and bound to particles in an air flow. The results obtained (see FIGS. 2 and 3) showed that the isocyanic acid efficiently gave a color reaction in the presence of 2,4,6-trihydroxyacetophenone impregnated as reagent on the sorbent surface and in the end filter device. The sorbents made of filter paper were analysed in a thin layer scanner (TLC scanner) at 475 nm and 550 nm, respectively. The FIGS. 2 and 3 clearly show the color change from reaction with isocyanic acid generated by pyrolysis of 50 µg of urea. Three filterpapers were impregnated with 2,4,6-trihydroxyacetophenone and then sprayed with a nitrite solution. One impregnated strip (2) was exposed to isocyanic acid (ICA), which have been generated by thermolysis of 50 µg of urea. The strips were illuminated by light (475 nm (FIG. 2), and 550 nm (FIG. 3), respectively), and the intensity of reflected light was measured with a TLC-scanner (Thin Layer Chromatography scanner).

The sorbent surface of a strip was also prepared with different components as disclosed in Examples 1-9 below, and tests performed with these strips have shown that the most distinct color changes were found at 475 nm with the reagents 2,4-dihydroxybenzophenone, 2,3,4-trihydroxybenzophenone, 1,3,5-trihydroxybenzene and 2,4,6-tri-hydroxyacetophenone.

Example 1

1,3-dihydroxybenzene (0.5 g) was dissolved in a mixture of acetonitrile (180 ml) and 1,2-dimethoxyethane (70 ml). To this solution was added 3.0 ml of a solution of sodium nitrite (3.0 g), ammonium acetate (0.15 g) in water (10 ml). The mixture was filtered and used to impregnate filter paper strips, which were dried in air before they were exposed to isocyanates.

Example 2

2,3,4-trihydroxybenzophenone (0.12 g) was dissolved in acetonitrile (18 ml) and 1,2-dimethoxyethane (7 ml). To this solution was added 0.5 ml of a solution of sodium nitrite (3.0 g), ammonium acetate (0.15 g) in water (10 ml). The mixture was filtered and used to impregnate filter paper strips which were dried in air before use.

Example 3

1,3,5-trihydroxybenzene (0.25 g) was dissolved in acetonitrile (90 ml) and 1,2-dimethoxyethane (35 ml). To this solution was added 1.5 ml of a solution of sodium nitrite (3.0 g), ammonium acetate (0.15 g) in water (10 ml). The mixture was filtered and used to impregnate filter paper strips, which were dried in air before use.

Example 4

2,4-dihydroxybenzophenone (1.7 g) was dissolved in a mixture of acetonitrile (5.0 ml) and 1,2-dimethoxyethane (1.0 ml). The filter paper strips were impregnated in this solution, dried in air. When dry they were each sprayed with a solution of 160 µl of the nitrite solution in Example 1 diluted to 460 µl. The strips were then used directly.

Example 5

2,4,6-trihydroxyacetophenone (0.5 g) was dissolved in a mixture of acetonitrile (3.0 ml) and 1,2-dimethoxyethane (0.6 ml). The filter paper strips were impregnated in this solution, dried and sprayed with 460 µl of the nitrite solution in Example 3. The strips were used directly.

Example 6

2,4,6-trimethoxyacetophenone (2.5 g) was dissolved in a mixture of acetonitrile (7.0 ml) and 1,2-dimethoxyethane (1.5 ml). The filter paper strips were impregnated with this solution and dried. The strips were sprayed with a mixture of 460 µl of the nitrite solution (see Example 3), and 200 µl of a 4M solution of zinc chloride, and used immediately.

Example 7

1,3-dihydroxynaphtalene (1.6 g) is dissolved in a mixture of acetonitrile (6.0 ml) and 1,2-dimethoxyethane (1.0 ml). Filter paper strips are impreganted with this solution and dried. The strips are the sprayed with the mixture of 460 µl of the nitrite solution and 200 µl of the zinc solution in Example 6 before use.

Example 8

1,3-dihydroxyantracene (1.5 g) is dissolved in a mixture of acetonitrile (6.0 ml) and 1,2-dimethoxyethane (1.0 ml). Filter paper strips are impregnated with this solution and dried. They are sprayed with 460 µl of the nitrite solution in Example 4.

Example 9

1,3-dihydroxyphenanthrene (0.5 g) is dissolved in a mixture of actonitrile (3.0 ml) and 1,2-dimethoxyethane (0.5 ml). Filter paper strips are impregnated, dried and then sprayed according to Example 8.

REFERENCES

1. Reilly. D. A., Analyst 93, 178-85.
2. Patent G.B. 1163647 (1969).
3. Eur. Pat. Appl. 180655, 14 May 1986.
4. Zhurnal Organischeskoi Khimi 23(8).
5. Eur. Pat. Appl. 1195411, 10 April 2002.
6. PCT Int. Appl. 2002068540, 06 Sep. 2002.
7. U.S. Pat. No. 5,976,881—Filed May 28, 1992—Colormetric Laboratories, Inc.

The invention claimed is:

1. A sampling device for analysis of isocyanate, aminoisocyanate, isothiocyanate, or amine present in an air flow intended to pass through the sampling device, wherein the sampling device comprises:
   a) an adsorption device adapted for the passage of the air flow and provided with a sorbent surface impregnated with at least one reagent in the form of:
   a benzene compound having the structure a naphtalene compound having the structure an anthracene compound having the structure or a phenanthrene compound having the structure wherein R is H, $CH_3$, $C_2H_5$, $C_3H_7$, $C_4H_9$, $C_5H_{11}$, $C_6H_{14}$, $C_6H_5$, or $C_{10}H_8$; wherein $X_1$, $X_2$, $X_3$, and $X_4$ are similar or nonsimilar and selected from R, OH, OR, COR, CONHR, $CO_2R$, and OCOR; wherein k is one or more of H, $SO_3H$, $SO_3Me^+$ (wherein $Me^+$ is $Li^+$, $Na^+$, or $K^+$), OH, OR, R, COR, $CO_2R$, $CO_2H$, OCOR, $NO_2$, or SR with at least one color developing agent, wherein said sorbent surface is not a filter;
   b) a light source for emission of light onto the sorbent surface; and
   c) a detector for detection of reflected light from the sorbent surface.

2. A sampling device according to claim 1, further comprising an end filter device also impregnated with said at least one reagent and said at least one color developing agent for reaction with said isocyanate present in the particle phase of the air flow, wherein said isocyanate in the gas phase of the air flow is reacted on said sorbent surface in the adsorption device.

3. A sampling device according to claim 1, wherein the adsorption device is tubular in the form, and the proportion of the length to the inner diameter being greater than 5.

4. A sampling device according to claim 3, wherein the sorbent surface is present on the inner wall of the adsorption device; on a strip to be suspended in the interior of the adsorption device, or on a movable disc or sheet to be brought to pass an opening in the wall of the adsorption device.

5. A sampling device according to claim 1, wherein the color developing agent is an ammonium nitrite compound or an alkali metal nitrite compound.

6. A sampling device according to claim 5, wherein the device is adapted to keep the sorbent surface moistened.

7. A sampling device according to claim 1, further comprising $Zn^{2+}$, $Co^{2+}$, $Fe^{2+}$, $Cr^{2+}$, $Cu^{2+}$ or $Mg^{2+}$ on the sorbent surface.

8. A sampling device according to claim 2, wherein the adsorption device has an upper end with an air inlet and a lower end which is connected to an upper end of the end filter device, the end filter device having a lower end with an air outlet.

9. A sampling device according to claim 8, wherein the sampling device is inverted in such a manner that the air inlet is arranged in the lower end of the end filter device and that the air outlet is arranged in the upper end of the adsorption device.

10. A sampling device according to claim 8, further comprising a pump or suction device to provide the air flow through the adsorption device and the end filter device, wherein the pump or suction device is connected either to the adsorption device or to the end filter device.

11. A sampling device according to claim 10, wherein the pump or suction device is connected to the lower end of the end filter device.

12. A sampling device according to claim 11, wherein the pump or suction device is a vacuum tube or a displacement pump.

13. A sampling device according to claim 1, wherein the light source is a light emitting diode or a laser source and the detector is a photomultiplier or a photodiode.

14. A sampling device according to claim 2, wherein the end filter device is formed as a substantially flat cylinder having a diameter which is greater than or equal to that of the adsorption device, wherein the device contains particles which are coated with the reagent and the color developing agent, and wherein the particles comprise pores having an average pore diameter of 0.1-20 μm.

15. A sampling device according to claim 1, wherein the concentration of the reagent on the sorbent surface is 0.05-40 mg/cm$^2$, the concentration of the color developing agent on the sorbent surface is 0.005-0.4 mmol/cm$^2$ and the concentration of divalent metal ions, if present, on the sorbent surface is 0.005-0.4 mmol/cm$^2$.

16. A sampling device according to claim 2, wherein the sorbent surface area is 0.25-5 cm².

17. A sampling device according to claim 2, wherein the adsorption device and the end filter device are enclosed in a uniform casing having a closable air inlet and a closable air outlet.

18. A sampling device according to claim 1, wherein the reagent is dihydroxybenzophenone, 2,3,4-trihydroxybenzophenone, 1,3,5-trihydroxybenzene, 2,4,6-trihydroxyacetophenone, 1,3-dihydroxynaphthalene, 1,3-dihydroxyanthracene, or 1,3-dihydroxyphenanthrene.

19. A kit comprising a plurality of sampling devices for taking samples from a plurality of different substances at the same time or at different points of time, the reagent in each sampling device being selected for the substance with which it is to react in the air flow, wherein each of said sampling devices comprises:

a) an adsorption device adapted for the passage of the air flow and provided with a sorbent surface impregnated with at least one reagent in the form of:

a benzene compound having the structure a naphtalene compound having the structure an anthracene compound having the structure or a phenanthrene compound having the structure wherein R is H, $CH_3$, $C_2H_5$, $C_3H_7$, $C_4H_9$, $C_5H_{11}$, $C_6H_{14}$, $C_6H_5$, or $C_{10}H_8$; wherein $X_1$, $X_2$, $X_3$, and $X_4$ are similar or nonsimilar and selected from R, OH, OR, COR, CONHR, $CO_2R$, and OCOR; wherein k is one or more of H, $SO_3H$, $SO_3Me^+$ (wherein $Me^+$ is $Li^+$, $Na^+$, or $K^+$), OH, OR, R, COR, $CO_2R$, $CO_2H$, OCOR, $NO_2$, or SR with at least one color developing agent, wherein said sorbent surface is not a filter;

b) a light source for emission of light onto the sorbent surface; and c) a detector for detection of reflected light from the sorbent surface.

20. A method for preparation of a sampling device, wherein the sampling device comprises:

a) an adsorption device adapted for the passage of the air flow and provided with a sorbent surface impregnated with at least one reagent in the form of:

a benzene compound having the structure a naphtalene compound having the structure an anthracene compound having the structure

-continued or a phenanthrene compound having the structure wherein R is H, $CH_3$, $C_2H_5$, $C_3H_7$, $C_4H_9$, $C_5H_{11}$, $C_6H_{14}$, $C_6H_5$, or $C_{10}H_8$; wherein $X_1$, $X_2$, $X_3$, and $X_4$ are similar or nonsimilar and selected from R, OH, OR, COR, CONHR, $CO_2R$, and OCOR; wherein k is one or more of H, $SO_3H$, $SO_3Me^+$ (wherein $Me^+$ is $Li^+$, $Na^+$, or $K^+$), OH, OR, R, COR, $CO_2R$, $CO_2H$, OCOR, $NO_2$, or SR with at least one color developing agent, wherein said sorbent surface is not a filter;

b) a light source for emission of light onto the sorbent surface; and c) a detector for detection of reflected light from the sorbent surface the method comprising:

dissolving the reagent in at least one organic solvent, wherein optionally at most 35%, preferably 20-30% (by volume), of the solvent is replaced with polyethylene glycol ether having the formula $RO-(CH_2CH_2O)_nR$, wherein n=0-4 and $R=CH_3$ or $C_2H_5$, adding the dissolved reagent to the sorbent surface, adding the color developing agent to the sorbent surface, and optionally adding divalent metal ions to the sorbent surface.

21. A method for analysis of a substance which is selected from the group consisting of isocyanates, aminoisocyanates, isothiocyanates, and amines, and which is present in both the gas and particle phase in an air flow, by means of a sampling device comprising:

a) an adsorption device adapted for the passage of the air flow and provided with a sorbent surface impregnated with at least one reagent in the form of:

a benzene compound having the structure a naphtalene compound having the structure an anthracene compound having the structure or a phenanthrene compound having the structure wherein R is H, $CH_3$, $C_2H_5$, $C_3H_7$, $C_4H_9$, $C_5H_{11}$, $C_6H_{14}$, $C_6H_5$, or $C_{10}H_8$; wherein $X_1$, $X_2$, $X_3$, and $X_4$ are similar or nonsimilar and selected from R, OH, OR, COR, CONHR, $CO_2R$, and OCOR; wherein k is one or more of H, $SO_3H$, $SO_3Me^+$ (wherein $Me^+$ is $Li^+$, $Na^+$, or $K^+$), OH, OR, R, COR, $CO_2R$, $CO_2H$, OCOR, $NO_2$, or SR with at least one color developing agent, wherein said sorbent surface is not a filter;

b) a light source for emission of light onto the sorbent surface;

c) a detector for detection of reflected light from the sorbent surface; and d) an end filter device also impregnated with said at least one reagent and said at least one color developing agent for reaction with said isocyanate present in the particle phase of the air flow, wherein said isocyanate in the gas phase of the air flow is reacted on said sorbent surface in the adsorption device;

the method comprising the steps of passing the air flow through the adsorption device and the end filter device by means of the pump or suction device for adsorption and reaction therein of the substance in both gas phase and particle phase, wherein the substances to analyse in the gas phase of the air flow are hydrolyzed by the water present to amines on the sorbent surface, which then are diazotized by the color developing agent impregnated on the substrate surface forming diazonium salts, which in turn then are coupled with the reagent impregnated on the substrate surface forming a color reaction, wherein light in the wavelength of 300-800 nm is emitted from a light source onto the sorbent surface on which the color reaction has taken place, and wherein light reflected from the sorbent surface is detected with a detector and the type and concentration of said substance in the gas phase of the air flow is determined, and wherein the type and concentration of said substance in the particle phase of the air flow is determined by analysis of the end filter device.

22. Method according to claim 21, wherein the method according to claim 20 is performed before the method for analysis is initiated.

23. A method according to claim 22, characterized in that an air flow of 0.01-5000 ml/min is passed through the sampling device.

24. The sampling device according to claim 1, wherein the sorbent surface is a pad.

25. A sampling device according to claim 2, wherein:
the adsorption device is tubular in form, the proportion of the length to the inner diameter being superior to 5;
the sorbent surface is present on the inner wall of the adsorption device; on a strip to be suspended in the interior of the adsorption device, or on a movable disc or sheet to be brought to pass an opening in the wall of the adsorption device;
the color developing agent is an ammonium nitrite compound or an alkali metal nitrite compound;
the sorbent surface is kept moistened;
divalent metal ions of $Zn^{2+}$, $Co^{2+}$, $Fe^{2+}$, $Cr^{2+}$, $Cu^{2+}$ or $Mg^{2+}$ also are present on the sorbent substrate; and
the reagent is dihydroxybenzophenone, 2,3,4-trihydroxybenzophenone, 1,3,5-trihydroxybenzene, 2,4,6-trihydroxyacetophenone, 1,3-dihydroxynaphthalene, 1,3-dihydroxyanthracene, or 1,3-dihydroxyphenanthrene.

26. A kit comprising a plurality of sampling devices for taking samples from a plurality of different substances at the same time or at different points of time, the reagent in each sampling device being selected for the substance with which it is to react in the air flow, wherein each of said sampling devices comprises:
a) an adsorption device adapted for the passage of the air flow and provided with a sorbent surface impregnated with at least one reagent in the form of:
a benzene compound having the structure a naphtalene compound having the structure an anthracene compound having the structure or a phenanthrene compound having the structure wherein R is H, $CH_3$, $C_2H_5$, $C_3H_7$, $C_4H_9$, $C_5H_{11}$, $C_6H_{14}$, $C_6H_5$, or $C_{10}H_8$; wherein $X_1$, $X_2$, $X_3$, and $X_4$ are similar or nonsimilar and selected from R, OH, OR, COR, CONHR, $CO_2R$, and OCOR; wherein k is one or more of H, $SO_3H$, $SO_3Me^+$ (wherein $Me^+$ is $Li^+$, $Na^+$, or $K^+$), OH, OR, R, COR, $CO_2R$, $CO_2H$, OCOR, $NO_2$, or SR with at least one color developing agent, wherein said sorbent surface is not a filter;
b) a light source for emission of light onto the sorbent surface;
c) a detector for detection of reflected light from the sorbent surface; and
d) an end filter device also impregnated with said at least one reagent and said at least one color developing agent for reaction with said isocyanate present in the particle phase of the air flow, wherein said isocyanate in the gas phase of the air flow is reacted on said sorbent surface in the adsorption device; and
wherein the adsorption device is tubular in form, the proportion of the length to the inner diameter being superior to 5;
the sorbent surface is present on the inner wall of the adsorption device; on a strip to be suspended in the interior of the adsorption device, or on a movable disc or sheet to be brought to pass an opening in the wall of the adsorption device;
the color developing agent is an ammonium nitrite compound or an alkali metal nitrite compound;
the sorbent surface is kept moistened;
divalent metal ions of $Zn^{2+}$, $Co^{2+}$, $Fe^{2+}$, $Cr^{2+}$, $Cu^{2+}$ or $Mg^{2+}$ also are present on the sorbent substrate; and
the reagent is dihydroxybenzophenone, 2,3,4-trihydroxybenzophenone, 1,3,5-trihydroxybenzene, 2,4,6-trihydroxyacetophenone, 1,3-dihydroxynaphthalene, 1,3-dihydroxyanthracene, or 1,3-dihydroxyphenanthrene.

27. A kit comprising a plurality of sampling devices for taking samples from a plurality of the different substances at the same time or at different points of time, the reagent in each sampling device being selected for the substance with which it is to react in the air flow, wherein each of said sampling devices comprises:
  a) an adsorption device adapted for the passage of the air flow and provided with a sorbent surface impregnated with at least one reagent in the form of:
    a benzene compound having the structure a naphtalene compound having the structure an anthracene compound having the structure or a phenanthrene compound having the structure wherein R is H, $CH_3$, $C_2H_5$, $C_3H_7$, $C_4H_9$, $C_5H_{11}$, $C_6H_{14}$, $C_6H_5$, or $C_{10}H_8$ wherein $X_1$, $X_2$, $X_3$, and $X_4$ are similar or nonsimilar and selected from R, OH, OR, COR, CONHR, $CO_2R$, and OCOR; wherein k is one or more of H, $SO_3H$, $SO_3Me^+$ (wherein $Me^+$ is $Li^+$, $Na^+$, or $K^+$), OH, OR, R, COR, $CO_2R$, $CO_2H$, OCOR, $NO_2$, or SR with at least one color developing agent, wherein said sorbent surface is not a filter;
  b) a light source for emission of light onto the sorbent surface;
  c) a detector for detection of reflected light from the sorbent surface; and
wherein the concentration of the reagent on the sorbent surface is 0.05-40 mg/cm², the concentration of the color developing agent on the sorbent surface is 0.005-0.4 mmol/cm² and the concentration of divalent metal ions, if present, on the sorbent surface is 0.005-0.4 mmol/cm².

28. A method for preparation of a sampling device, the device comprising:
  a) an adsorption device adapted for the passage of the air flow and provided with a sorbent surface impregnated with at least one reagent in the form of:
    a benzene compound having the structure a naphtalene compound having the structure an anthracene compound having the structure or a phenanthrene compound having the structure wherein R is H, CH$_3$, C$_2$H$_5$, C$_3$H$_7$, C$_4$H$_9$, C$_5$H$_{11}$, C$_6$H$_{14}$, C$_6$H$_5$, or C$_{10}$H$_8$; wherein X$_1$, X$_2$, X$_3$, and X$_4$ are similar or nonsimilar and selected from R, OH, OR, COR, CONHR, CO$_2$R, and OCOR; wherein k is one or more of H, SO$_3$H, SO$_3$Me$^+$ (wherein Me$^+$ is Li$^+$, Na$^+$, or K$^+$), OH, OR, R, COR, CO$_2$R, CO$_2$H, OCOR, NO$_2$, or SR with at least one color developing agent, wherein said sorbent surface is not a filter;

b) a light source for emission of light onto the sorbent surface;

c) a detector for detection of reflected light from the sorbent surface; and d) an end filter device also impregnated with said at least one reagent and said at least one color developing agent for reaction with said isocyanate present in the particle phase of the air flow, wherein said isocyanate in the gas phase of the air flow is reacted on said sorbent surface in the adsorption device; and wherein the adsorption device is tubular in form, the proportion of the length to the inner diameter being superior to 5;

the sorbent surface is present on the inner wall of the adsorption device; on a strip to be suspended in the interior of the adsorption device, or on a movable disc or sheet to be brought to pass an opening in the wall of the adsorption device;

the color developing agent is an ammonium nitrite compound or an alkali metal nitrite compound;

the sorbent surface is kept moistened;

divalent metal ions of Zn$^{2+}$, Co$^{2+}$, Fe$^{2+}$, Cr$^{2+}$, Cu$^{2+}$ or Mg$^{2+}$ also are present on the sorbent substrate; and the reagent is dihydroxybenzophenone, 2,3,4-trihydroxybenzophenone, 1,3,5-trihydroxybenzene, 2,4,6-trihydroxyacetophenone, 1,3-dihydroxynaphthalene, 1,3-dihydroxyanthracene, or 1,3-dihydroxyphenanthrene;

the method comprising the steps of:

dissolving the reagent in at least one organic solvent, wherein optionally at most 35% (by volume) of the solvent is replaced with polyethylene glycol ether having the formula RO—(CH$_2$CH$_2$O)$_n$R, wherein n=0-4 and R=CH$_3$ or C$_2$H$_5$;

adding the dissolved reagent to the sorbent surface;

adding the color developing agent to the sorbent surface; and optionally adding divalent metal ions to the sorbent surface.

29. A method for preparation of a sampling device, the device comprising:

a) an adsorption device adapted for the passage of the air flow and provided with a sorbent surface impregnated with at least one reagent in the form of:

a benzene compound having the structure a naphtalene compound having the structure an anthracene compound having the structure or a phenanthrene compound having the structure wherein R is H, CH$_3$, C$_2$H$_5$, C$_3$H$_7$, C$_4$H$_9$, C$_5$H$_{11}$, C$_6$H$_{14}$, C$_6$H$_5$, or C$_{10}$H$_8$; wherein X$_1$, X$_2$, X$_3$, and X$_4$ are similar or nonsimilar and selected from R, OH, OR, COR, CONHR, CO$_2$R, and OCOR; wherein k is one or more of H, SO$_3$H, SO$_3$Me$^+$ (wherein Me$^+$ is Li$^+$, Na$^+$, or K$^+$), OH, OR, R, COR, CO$_2$R, CO$_2$H, OCOR, NO$_2$, or SR with at least one color developing agent, wherein said sorbent surface is not a filter;

b) a light source for emission of light onto the sorbent surface;

c) a detector for detection of reflected light from the sorbent surface; and wherein the concentration of the reagent on the sorbent surface is 0.05-40 mg/cm$^2$, the concentration of the color developing agent on the sorbent surface is 0.005-0.4 mmol/cm$^2$ and the concentration of divalent metal ions, if present, on the sorbent surface is 0.005-0.4 mmol/cm$^2$;

wherein method comprising the steps of:

dissolving the reagent in at least one organic solvent, wherein optionally at most 35% (by volume) of the solvent is replaced with polyethylene glycol ether having the formula RO—(CH$_2$CH$_2$O)$_n$R, wherein n=0-4 and R=CH$_3$ or C$_2$H$_5$;

adding the dissolved reagent, to the sorbent surface;

adding color developing agent to the sorbent surface; and optionally adding divalent metal ions to the sorbent surface.

30. A method for analysis of a substance which is selected from the group consisting of isocyanates, aminoisocyanates, isothiocyanates, and amines, and which is present in both the gas and particle phase in an air flow, by means of a sampling device comprising:
a) an adsorption device adapted for the passage of the air flow and provided with a sorbent surface impregnated with at least one reagent in the form of:
a benzene compound having the structure a naphtalene compound having the structure an anthracene compound having the structure or a phenanthrene compound having the structure wherein R is H, $CH_3$, $C_2H_5$, $C_3H_7$, $C_4H_9$, $C_5H_{11}$, $C_6H_{14}$, $C_6H_5$, or $C_{10}H_8$; wherein $X_1$, $X_2$, $X_3$, and $X_4$ are similar or nonsimilar and selected from R, OH, OR, COR, CONHR, $CO_2R$, and OCOR; wherein k is one or more of H, $SO_3H$, $SO_3Me^+$ (wherein $Me^+$ is $Li^+$, $Na^+$, or $K^+$), OH, OR, R, COR, $CO_2R$, $CO_2H$, OCOR, $NO_2$, or SR with at least one color developing agent, wherein said sorbent surface is not a filter;
b) a light source for emission of light onto the sorbent surface;
c) a detector for detection of reflected light from the sorbent surface; and
d) an end filter device also impregnated with said at least one reagent and said at least one color developing agent for reaction with said isocyanate present in the particle phase of the air flow, wherein said isocyanate in the gas phase of the air flow is reacted on said sorbent surface in the adsorption device; and
wherein the adsorption device is tubular in form, the proportion of the length to the inner diameter being superior to 5;
the sorbent surface is present on the inner wall of the adsorption device; on a strip to be suspended in the interior of the adsorption device, or on a movable disc or sheet to be brought to pass an opening in the wall of the adsorption device;
the color developing agent is an ammonium nitrite compound or an alkali metal nitrite compound;
the sorbent surface is kept moistened;
divalent metal ions of $Zn^{2+}$, $Co^{2+}$, $Fe^{2+}$, $Cr^{2+}$, $Cu^{2+}$ or $Mg^{2+}$ also are present on the sorbent substrate; and
the reagent is dihydroxybenzophenone, 2,3,4-trihydroxybenzophenone, 1,3,5-trihydroxybenzene, 2,4,6-trihydroxyacetophenone, 1,3-dihydroxynaphthalene, 1,3-dihydroxyanthracene, or 1,3-dihydroxyphenanthrene;
the method comprising the steps of passing the air flow through the adsorption device and the end filter device by means of the pump or suction device for adsorption and reaction therein of the substance in both gas phase and particle phase, wherein the substances to analyse in the gas phase of the air flow are hydrolyzed by the water present to amines on the sorbent surface, which then are diazotized by the color developing agent impregnated on the substrate surface forming diazonium salts, which in turn then are coupled with the reagent impregnated on the substrate surface forming a color reaction, wherein light in the wavelength of 300-800 nm is emitted from a light source onto the sorbent surface on which the color reaction has taken place, and wherein light reflected from the sorbent surface is detected with a detector and the type and concentration of said substance in the gas phase of the air flow is determined, and wherein the type and concentration of said substance in the particle phase of the air flow is determined by analysis of the end filter device.

31. A method for analysis of a substance which is selected from the group consisting of isocyanates, aminoisocyanates, isothiocyanates, and amines, and which is present in both the gas and particle phase in an air flow, by means of a sampling device comprising:
a) an adsorption device adapted for the passage of the air flow and provided with a sorbent surface impregnated with at least one reagent in the form of:
a benzene compound having the structure a naphtalene compound having the structure an anthracene compound having the structure or a phenanthrene compound having the structure wherein R is H, $CH_3$, $C_2H_5$, $C_3H_7$, $C_4H_9$, $C_5H_{11}$, $C_6H_{14}$, $C_6H_5$, or $C_{10}H_8$; wherein $X_1$, $X_2$, $X_3$, and $X_4$ are similar or nonsimilar and selected from R, OH, OR, COR, CONHR, $CO_2R$, and OCOR; wherein k is one or more of H, $SO_3H$, $SO_3Me^+$ (wherein $Me^+$ is $Li^+$, $Na^+$, or $K^+$), OH, OR, R, COR, $CO_2R$, $CO_2H$, OCOR, $NO_2$, or SR with at least one color developing agent, wherein said sorbent surface is not a filter;
b) a light source for emission of light onto the sorbent surface;
c) a detector for detection of reflected light from the sorbent surface; and
d) an end filter device also impregnated with said at least one reagent and said at least one color developing agent for reaction with said isocyanate present in the particle phase of the air flow, wherein said isocyanate in the gas phase of the air flow is reacted on said sorbent surface in the adsorption device; and
wherein the concentration of the reagent on the sorbent surface is 0.05-40 $mg/cm^2$, the concentration of the color developing agent on the sorbent surface is 0.005-0.4 $mmol/cm^2$ and the concentration of divalent metal ions, if present, on the sorbent surface is 0.005-0.4 $mmol/cm^2$;
the method comprising the steps of passing the air flow through the adsorption device and the end filter device by means of the pump or suction device for adsorption and reaction therein of the substance in both gas phase and particle phase, wherein the substances to analyse in the gas phase of the air flow are hydrolyzed by the water present to amines on the sorbent surface, which then are diazotized by the color developing agent impregnated on the substrate surface forming diazonium salts, which in turn then are coupled with the reagent impregnated on the substrate surface forming a color reaction, wherein light in the wavelength of 300-800 nm is emitted from a light source onto the sorbent surface on which the color reaction has taken place, and wherein light reflected from the sorbent surface is detected with a detector and the type and concentration of said substance in the gas phase of the air flow is determined, and wherein the type and concentration of said substance in the particle phase of the air flow is determined by analysis of the end filter device.

32. A method for analysis of a substance which is selected from the group consisting of isocyanates, aminoisocyanates, isothiocyanates, and amines, and which is present in both the gas and particle phase in an air flow, by means of a plurality of sampling devices a plurality of sampling devices for taking samples from a plurality of different substances at the same time or at different points of time, the reagent in each sampling device being selected for the substance with which it is to react in the air flow, wherein each of said sampling devices comprises:
a) an adsorption device adapted for the passage of the air flow and provided with a sorbent surface impregnated with at least one reagent in the form of:
a benzene compound having the structure a naphtalene compound having the structure an anthracene compound having the structure or a phenanthrene compound having the structure wherein R is H, $CH_3$, $C_2H_5$, $C_3H_7$, $C_4H_9$, $C_5H_{11}$, $C_6H_{14}$, $C_6H_5$, or $C_{10}H_8$; wherein $X_1$, $X_2$, $X_3$, and $X_4$ are similar or nonsimilar and selected from R, OH, OR, COR, CONHR, $CO_2R$, and OCOR; wherein k is one or more of H, $SO_3H$, $SO_3Me^+$ (wherein $Me^+$ is $Li^+$, $Na^+$, or $K^+$), OH, OR, R, COR, $CO_2R$, $CO_2H$, OCOR, $NO_2$, or SR with at least one color developing agent, wherein said sorbent surface is not a filter;

b) a light source for emission of light onto the sorbent surface;

c) a detector for detection of reflected light from the sorbent surface; and d) an end filter device also impregnated with said at least one reagent and said at least one color developing agent for reaction with said isocyanate present in the particle phase of the air flow, wherein said isocyanate in the gas phase of the air flow is reacted on said sorbent surface in the adsorption device;

the method comprising the steps of passing the air flow through the adsorption device and the end filter device by means of the pump or suction device for adsorption and reaction therein of the substance in both gas phase and particle phase, wherein the substances to analyse in the gas phase of the air flow are hydrolyzed by the water present to amines on the sorbent surface, which then are diazotized by the color developing agent impregnated on the substrate surface forming diazonium salts, which in turn then are coupled with the reagent impregnated on the substrate surface forming a color reaction, wherein light in the wavelength of 300-800 nm is emitted from a light source onto the sorbent surface on which the color reaction has taken place, and wherein light reflected from the sorbent surface is detected with a detector and the type and concentration of said substance in the gas phase of the air flow is determined, and wherein the type and concentration of said substance in the particle phase of the air flow is determined by analysis of the end filter device.

33. The sampling device according to claim 25, wherein the sorbent surface is a pad.

34. The sampling device according to claim 15, wherein the sorbent surface is a pad.

35. The sampling device according to claim 5, wherein the color developing agent is $NH_4NO_2$, $LiNO_2$, $NaNO_2$, or $KNO_2$.

36. The sampling device according to claim 12, wherein the pump is a hose pump, diaphragm pump, injection pump, or gear-type pump.

* * * * *

UNITED STATES PATENT AND TRADEMARK OFFICE
CERTIFICATE OF CORRECTION

PATENT NO.       : 8,034,624 B2
APPLICATION NO.  : 12/299940
DATED            : October 11, 2011
INVENTOR(S)      : Gunnar Skarping et al.

Page 1 of 1

It is certified that error appears in the above-identified patent and that said Letters Patent is hereby corrected as shown below:

In the Specification

Column 5, line 47, "naphtyidiisocyanate" should read --naphtyldiisocyanate--; and In the Claims Column 14, claim 19, line 14, "$C_{10}H^8$" should read --$C_{10}H_8$--.

Signed and Sealed this
Twenty-fifth Day of June, 2013

Teresa Stanek Rea
*Acting Director of the United States Patent and Trademark Office*